(12) United States Patent
Pickford et al.

(10) Patent No.: US 7,695,522 B2
(45) Date of Patent: Apr. 13, 2010

(54) METAL IMPLANTS

(75) Inventors: Martin Edward Lee Pickford, Southampton (GB); Andrew Derek Turner, Abingdon (GB)

(73) Assignee: Accentus plc, Oxfordshire (GB)

( * ) Notice: Subject to any disclaimer, the term of this patent is extended or adjusted under 35 U.S.C. 154(b) by 0 days.

(21) Appl. No.: 10/501,538

(22) PCT Filed: Mar. 25, 2003

(86) PCT No.: PCT/GB03/01264

§ 371 (c)(1),
(2), (4) Date: Jul. 16, 2004

(87) PCT Pub. No.: WO03/089023

PCT Pub. Date: Oct. 30, 2003

(65) Prior Publication Data

US 2005/0119743 A1  Jun. 2, 2005

(30) Foreign Application Priority Data

Apr. 16, 2002  (GB) ................... 0208642.9

(51) Int. Cl.
*A61F 2/28* (2006.01)
(52) U.S. Cl. ............... 623/23.53; 623/23.75; 623/1.42
(58) Field of Classification Search ............. 623/23.57
See application file for complete search history.

(56) References Cited

U.S. PATENT DOCUMENTS

| | | | |
|---|---|---|---|
| 4,027,393 A | 6/1977 | Ellis | |
| 4,263,681 A | 4/1981 | Notton | 3/1.91 |
| 4,336,617 A | 6/1982 | Shikita | 3/1.9 |
| 4,813,965 A | 3/1989 | Roberts | |
| 4,938,409 A | 7/1990 | Roberts | |
| 5,185,075 A * | 2/1993 | Rosenberg et al. | 205/234 |
| 5,454,886 A | 10/1995 | Burrell | |
| 5,482,731 A | 1/1996 | Vargas-Gutierrez | 427/2.27 |
| 5,492,763 A | 2/1996 | Barry | 428/457 |
| 5,695,857 A | 12/1997 | Burrell | |
| 5,770,255 A | 6/1998 | Burrell | |
| 6,113,636 A | 9/2000 | Ogle | 623/11.11 |
| 6,365,220 B1 | 4/2002 | Burrell | 427/2.1 |
| 6,663,634 B2 | 12/2003 | Ahrens | |
| 2002/0099449 A1 | 7/2002 | Speitling | |

FOREIGN PATENT DOCUMENTS

| | | |
|---|---|---|
| EP | 0257923 | 3/1988 |
| GB | 2073024 | 10/1981 |
| JP | 10158889 | 6/1998 |
| JP | 10168598 | 6/1998 |
| JP | 11181596 | 7/1999 |
| JP | 11229186 | 8/1999 |
| JP | 11236699 | 8/1999 |
| JP | 11343592 | 12/1999 |
| JP | 2005287985 A | 10/2005 |
| WO | 98/51231 A1 | 11/1998 |
| WO | 99/01089 | 1/1999 |
| WO | 00/51659 | 9/2000 |
| WO | 00/72777 A1 | 12/2000 |
| WO | 02/096475 A1 | 12/2002 |
| WO | 03/003938 A1 | 1/2003 |
| WO | 03/089023 A1 | 10/2003 |

OTHER PUBLICATIONS

English language abstract of JP10158889, Jun. 16, 1998.
English language abstract of JP10168598, Jun. 23, 1998.
English language abstract of JP11181596, Jul. 6, 1999.
English language abstract of JP11229186, Aug. 24, 1999.
English language abstract of JP11236699, Aug. 31, 1999.
English language abstract of JP11343592, Dec. 14, 1999.
English language abstract of JP 2005287985, Oct. 20, 2005.

* cited by examiner

*Primary Examiner*—David Isabella
*Assistant Examiner*—Christopher D Prone
(74) *Attorney, Agent, or Firm*—Tumey L.L.P.

(57) ABSTRACT

A metal implant for use in a surgical procedure is provided with a surface layer that is integral with the metal substrate, and which incorporates a biocidal material. The surface layer may be grown from the metal substrate, by anodizing, and the biocidal material incorporated in it by ion exchange. Alternatively the layer may be deposited by electroplating, followed by diffusion bonding so as to become integral with the metal substrate. In either case, silver is a suitable biocidal material; and both the release rate and the quantity of biocidal material should be low to avoid toxic effects on body cells. Electropolishing the surface before formation of the surface layer is also beneficial, and this may be achieved by electropolishing.

15 Claims, No Drawings

METAL IMPLANTS

This application is a national stage entry of PCT/GB03/01264 filed on Mar. 25, 2003 claiming foreign priority to 0208642.9, filed on Apr. 16, 2002.

This invention relates to metal implants for use in surgical procedures, and in particular to the introduction of a biocidal material into such implants to suppress or control infection.

BACKGROUND OF THE INVENTION

Various surgical procedures require the use of implants. For example cancerous bone may be removed, in prosthetic surgery, to be replaced by a metal implant. Such an implant may for example be of titanium alloy, which is very strong and relatively light. To ensure a hard-wearing surface the provision of a titanium nitride coating has been suggested. There is furthermore a risk of introducing infection when implanting such metal implants, and it has been suggested that metallic silver might be electroplated onto metal implants, the silver being a biocidal material that can control infection without causing toxic effects to the patient. However such coatings, whether of titanium nitride or silver, may be undercut due to corrosion from body fluids, so that the coating may detach from the implant, which may can increase wear and cause tissue damage.

SUMMARY OF THE INVENTION

According to the present invention there is provided an implant for use in a surgical procedure, the implant comprising a metal substrate and a surface layer that is integral with the metal substrate, the layer incorporating a biocidal metal deposited from a solution.

The invention also provides a method of producing such an implant.

DETAILED DESCRIPTION OF THE INVENTION

Such an integral surface layer may be generated by growing the layer from the metal itself, for example by an anodising process; or alternatively by depositing the layer for example by electroplating, followed by diffusion bonding so that the layer becomes integral with the metal of the implant. Anodising forms an adherent oxide layer, although if it is carried out in phosphoric acid then a phosphate may be formed. Such an adherent phosphate layer may also be modified to form a hydroxyapatite layer, which can stimulate bone growth.

The biocidal material should preferably be effective for at least 6 weeks, preferably for up to 6 months after surgery, and the release rate should be low to avoid toxic effects on body cells. Furthermore the total quantity of biocidal material is preferably also limited to minimize any toxic effects.

It is also desirable if the surface is highly polished before production of the surface layer. This may for example be achieved by electropolishing.

In principle, a range of different metals may be used for the biocidal metal. In particular, if the layer is a metal layer deposited by electroplating then it clearly must be stable to corrosion. Gold, platinum, iridium and palladium would be potentially suitable, although expensive; silver is preferable as it is not particularly soluble in body fluids due to the presence of chloride ions and the low solubility of silver chloride. If the surface layer contains the biocidal metal in ionic form, then a wider range of metals would be possible. In addition to the elements already mentioned, copper, tin, antimony, lead, bismuth and zinc might be used as ions combined into an insoluble matrix for example of metal oxide or metal phosphate. The rate of release would be controlled, in this case, primarily by the strength of the absorption of the metal ions in the matrix.

The metals that may be used to make such prosthetic implants are typically a form of stainless steel, a titanium alloy, or a cobalt/chromium alloy, although zirconium could also be used. The standard alloys for this purpose are titanium 90% with 6% aluminium and 4% vanadium (British standard 7252), or chromium 26.5-30%, molybdenum 4.5-7%, and the remainder cobalt (British standard 7252 part 4).

Preferably the implant is initially polished to provide a very smooth surface. Both stainless steel (chromium/iron/nickel) and cobalt/chromium alloy can be electro-polished using as electrolyte a mixture of phosphoric acid and glycerine, or a mixture of phosphoric acid and sulphuric acid. Titanium alloy can be electro-polished using acetic acid, or a mixture of nitric and hydrofluoric acids. Alternatively the implants might be subjected to a combination of anodic passivation with mechanical polishing, which may be referred to as electrolinishing, this process removing the oxide that protects surface roughness, the surface at that point then being electrochemically re-passivated, so producing a mirror-smooth finish. Various electrolytes are suitable for this purpose, including nitric acid mixed with sulphuric acid, sodium hydroxide, sodium phosphate, or sodium hydroxide mixed with sodium nitrate.

After polishing the surface of the metal, either silver deposition or surface conversion can take place. Considering surface conversion first, a layer of metal oxide or phosphate may be formed by anodising in a suitable electrolyte, so that the oxide or phosphate layer builds out from the surface of the metal. Biocidal metal ions can then be absorbed from an aqueous salt solution into the oxide or phosphate matrix, for example the ions $Ag^+$ or $Cu^{++}$. Cations of palladium, platinum or even ruthenium could be absorbed in a similar way. If desired, deposited silver, platinum or palladium ions could then be converted to metal, or deposited ruthenium ions converted to insoluble $RuO_2$, within the oxide or phosphate surface coating, this reaction being performed chemically or electrochemically or by light.

Considering now silver deposition, the coating should be thin to prevent toxic effects. A high degree of adherence to the underlying metal can be ensured by first removing the surface oxide layer by anodic etching, followed by a brief reversal of polarity in the presence of appropriate ions, so as to cover the surface with a thin coating of silver. This may be repeated to ensure there are no pin-holes. The plating electrolyte may include hydrofluoric acid, or may be an alkaline cyanide electroplating electrolyte. After deposition, the silver coating should be diffusion bonded so as to form an inter-metallic layer, by heating the implant to an elevated temperature. Typically it should be heated to above 800° C., preferably between 810° C. and 950° C., in an inert atmosphere for example of argon for a period of between 1 and 6 hours. This substantially eliminates the risk of coating delamination. However with titanium-based implants the temperature must not exceed 850° C. as titanium would undergo a phase change from alpha to beta form above this temperature.

In place of silver, other metals such as platinum or palladium may be electro-deposited and then thermally treated in a similar fashion so as to form an inter-metallic layer.

The invention will now be further and more particularly described, by way of example only.

A hip implant is made of titanium alloy (Ti/Al/V). The implant is cleaned ultrasonically using first acetone as the liquid phase, and then a 1 M aqueous solution of sodium hydroxide, and is then rinsed in de-ionised water. The cleaned implant is then immersed in a stirred 12 weight % solution of phosphoric acid, and is anodised for 2 hours at a maximum voltage of 10V and a maximum current of 10 mA/cm$^2$, so as to form a surface coating of titanium phosphate. It is then rinsed in de-ionised water again. The surface, which is initially pale grey, turns to a darker matt grey as a consequence of the anodising, with a slightly yellow hue.

The implant is then immersed in a stirred 0.1 M aqueous solution of silver nitrate, and left for 2 hours. As a result of ion exchange there is consequently some silver phosphate in the titanium phosphate coating. The implant is then ready to be implanted. During exposure to body fluids there will be a slow leaching of silver ions from the phosphate layer, so that any bacteria in the immediate vicinity of the implant are killed. Infection arising from the implant is therefore suppressed.

Experimental samples of this titanium alloy were cleaned, anodised to form a layer of titanium phosphate, and then subjected to ion exchange to form silver phosphate, following the procedure described above. One sample was placed in direct daylight for 110 hours; the exposed surface became darkened as a result of this exposure to daylight, indicating the formation of silver metal by photo-reduction. The other sample was immersed in a solvent containing a mixture of 4 M nitric acid and 0.5 M sodium fluoride (equivalent to hydrofluoric acid) to dissolve the coating. The dark grey surface coating was removed completely within 3 minutes, leaving a silver-grey finish. The resulting solution was analyzed for the presence of silver by atomic absorption spectrometry, and the concentration of silver was found to be equivalent to an average surface loading of 73 μg/cm$^2$.

The invention claimed is:

1. An implant for use in a surgical procedure, said implant comprising a metal substrate and a surface layer integral with said metal substrate, said surface layer comprising an anodized layer grown from the metal of said metal substrate by anodizing, said surface layer incorporating a biocidal metal in an ionic form, the biocidal metal ions being adsorbed into said surface layer by ion exchange, and the quantity of biocidal metal ions being such that the biocidal material is effective in suppressing infection after the surgical procedure, wherein said biocidal metal ions are silver ions, and wherein the concentration of said silver is equivalent to an average surface loading of 73 μg/cm$^2$.

2. An implant as claimed in claim 1 wherein said surface layer comprises a metal phosphate.

3. An implant as claimed in claim 2 wherein the surface of said implant is in a highly polished condition before provision of said surface layer.

4. An implant as claimed in claim 1 wherein the surface of said implant is in a highly polished condition before provision of said surface layer.

5. An implant as claimed in claim 1 wherein the biocidal material adsorbed into said surface layer is effective in suppressing infection for at least 6 weeks after the surgical procedure.

6. An implant for use in a surgical procedure, said implant comprising a metal substrate and a surface layer integral with said metal substrate, said surface layer comprising an anodized layer containing material selected from the group consisting of oxide, and phosphate, and being grown from the metal of said metal substrate by anodizing, wherein said anodized layer incorporates a biocidal metal adsorbed by ion exchange into said surface layer, and the quantity of biocidal metal ions being such that the biocidal material is effective in suppressing infection after the surgical procedure, wherein said biocidal metal ions are silver ions, and wherein the concentration of said silver is equivalent to an average surface loading of 73 μg/cm$^2$.

7. An implant as claimed in claim 6 wherein said surface layer comprises a metal phosphate.

8. An implant as claimed in claim 7 wherein the surface of said implant is in a highly polished condition before provision of said surface layer.

9. An implant as claimed in 6 wherein the surface of said implant is in a highly polished condition before provision of said surface layer.

10. An implant as claimed in claim 6 wherein the biocidal material adsorbed into said surface layer is effective in suppressing infection for at least 6 weeks after the surgical procedure.

11. An implant for use in a surgical procedure, said implant comprising a metal substrate and a surface layer integral with said metal substrate, said surface layer comprising a material selected from the group consisting of oxide, and phosphate, said surface layer further comprising an anodized layer grown from the metal of said metal substrate by anodizing and incorporating therein a biocidal metal adsorbed by ion exchange into said surface layer, and the quantity of biocidal metal ions being such that the biocidal material is effective in suppressing infection after the surgical procedure, wherein said biocidal metal ions are silver ions, and wherein the concentration of said silver is equivalent to an average surface loading of 73 μg/cm$^2$.

12. An implant as claimed in claim 11 wherein said surface layer comprises a metal phosphate.

13. An implant as claimed in claim 12 wherein the surface of said implant is in a highly polished condition before provision of said surface layer.

14. An implant as claimed in claim 11 wherein the surface of said implant is in a highly polished condition before provision of said surface layer.

15. An implant as claimed in claim 11 wherein the biocidal material adsorbed into said surface layer is effective in suppressing infection for at least 6 weeks after the surgical procedure.

* * * * *